United States Patent [19]

Siddens

[11] 4,407,760

[45] Oct. 4, 1983

[54] METHOD FOR THE PREPARATION OF DIFLUOROMETHOXYAROMATIC COMPOUNDS

[75] Inventor: Jack K. Siddens, Princeton Junction, N.J.

[73] Assignee: American Cyanamid Company, Stamford, Conn.

[21] Appl. No.: 420,169

[22] Filed: Sep. 20, 1982

[51] Int. Cl.$^3$ .................. C07C 121/75; C07C 43/225; C07C 69/712; C07C 79/35

[52] U.S. Cl. ........................... 260/465 F; 260/456 R; 260/456 P; 560/55; 560/254; 568/588; 568/649; 568/655; 568/656

[58] Field of Search ............ 260/465 F, 456 R, 456 P; 560/55, 254; 568/588, 649, 655, 656

[56] References Cited

U.S. PATENT DOCUMENTS 4,199,595  4/1980  Berkelhammer et al. .......... 424/304

*Primary Examiner*—Dolph H. Torrence
*Attorney, Agent, or Firm*—Thomas J. Monahan

[57] ABSTRACT

A method for the preparation of difluoromethoxyaromatic compounds which are useful intermediates for the preparation of pyrethroid pesticides. The method comprises alkylating a p-substituted phenol with excess chlorodifluoromethane at atmospheric or superatmospheric pressures in the presence of a base, water, and an inert water miscible organic solvent mixture.

9 Claims, No Drawings

METHOD FOR THE PREPARATION OF DIFLUOROMETHOXYAROMATIC COMPOUNDS

The invention herein described relates to a method for the preparation of certain difluoromethoxyaromatic compounds. These compounds are useful intermediates in the preparation of certain broad spectrum pyrethroid pesticides. The method comprises the alkylation of a p-substituted phenol with excess chlorodifluoromethane at atmospheric and superatmospheric pressure in the presence of a base, water, and an inert water miscible organic solvent mixture.

By way of background, pyrethroid pesticides are disclosed and claimed in U.S. Pat. No. 4,199,595. This patent is incorporated herein by way of reference. The preparation of pyrethroid pesticides conveniently involves certain of the difluoromethoxyaromatic compounds of the present invention. Pyrethroid pesticides are valuable and highly effective chemicals for the control of various insects and other pests, particularly those which cause significant economic damage to field crops and livestock. Some of the pyrethroids which are described in the above-referenced patent, and prepared using intermediates of the present invention, are broad spectrum pesticides. As such they are highly effective as contact and stomach poisons for ixodidae ticks and for a wide variety of insects, particularly Dipterous, Lepidopterous, Loleopterous and Homopterous insects. These pyrethroids are effective for the control of ixodidae and the protection of animals against attack by these organisms when administered to animals orally or parentally or applied thereto as a topical insecticide or acaricidal formulation.

In light of the foregoing discussion of the desirability of obtaining pyrethroid pesticides for the control of noxious pests, it is advantageous to obtain the chemical intermediates which are involved in the synthesis of these products. Accordingly, an object of this invention is to provide a method for the preparation of certain difluoromethoxyaromatic compounds which can be used in the preparation of pyrethroid pesticides. This object is manifest in the following description and particularly delineated in the appended claims.

A method for the preparation of certain difluoromethoxyaromatic compounds has been unexpectedly discovered. Such difluoromethoxyaromatic compounds are represented by structural formula-(I):

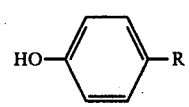
(I)

wherein R is selected from $C_1$–$C_3$ alkyl, halogen, nitro, or is the moiety

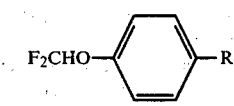

$R_1$ is —CN, —COOR$_2$, OH or OR$_3$, $R_2$ is $C_1$–$C_3$ alkyl, $R_3$ is tosyl, mesyl or $C_2$–$C_4$ alkanoyl.

A preferred group of compounds of formula-(I) may be graphically represented by structural formula-(Ia) below:

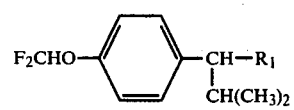
(Ia)

wherein $R_1$ is as hereinabove defined.

Another, more preferred group of compounds may be represented by structural formula-(Ib) below:

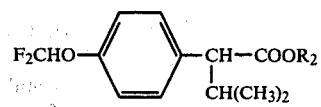
(Ib)

wherein $R_2$ is $CH_3$ or $C_2H_5$.

Of particular interest are the following compounds of formula-(I)

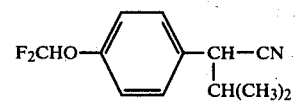

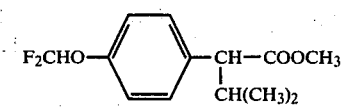

and

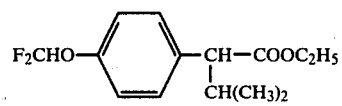

since these are valuable, and convenient intermediates for the preparation of broad spectrum pyrethroid pesticides.

Advantageously, a compound of formula-(I) may be prepared by reacting a phenol of formula-(II)

(II)

wherein R is as hereinabove defined, with chlorodifluoromethane at atmospheric and superatmospheric pressures in the presence of a base, an inert water miscible organic solvent mixture, water and benzyltriethylammonium chloride (BTEAC) until the reaction is essentially complete, and a compound of formula-(I) is obtained, as graphically illustrated below:

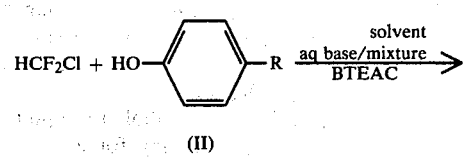
(II)

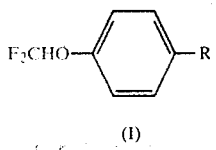

(I)

R is as hereinabove defined. As stated above, certain of the compounds of formula-(I) are useful and valuable intermediates for the preparation of pyrethroid type pesticides.

Thus, the compounds of formula-(Ia), $R_1$=CN or $COOR_2$, may be hydrolyzed to yield the corresponding acid [i.e., formula-(III)]. The acid [i.e., formula-(III)] is then converted to the acid chloride [i.e., formula-(IV)], and the acid chloride [i.e., formula-(IV)] is reacted with a benzyl alcohol represented by structural formula-(V) below:

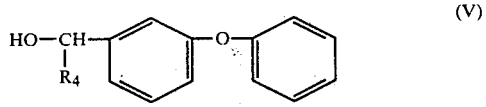

(V)

wherein $R_4$ is hydrogen or cyano, to yield the desired pyrethroid insecticide [i.e., formula-(VI)]. The above reaction sequence may be graphically illustrated as follows:

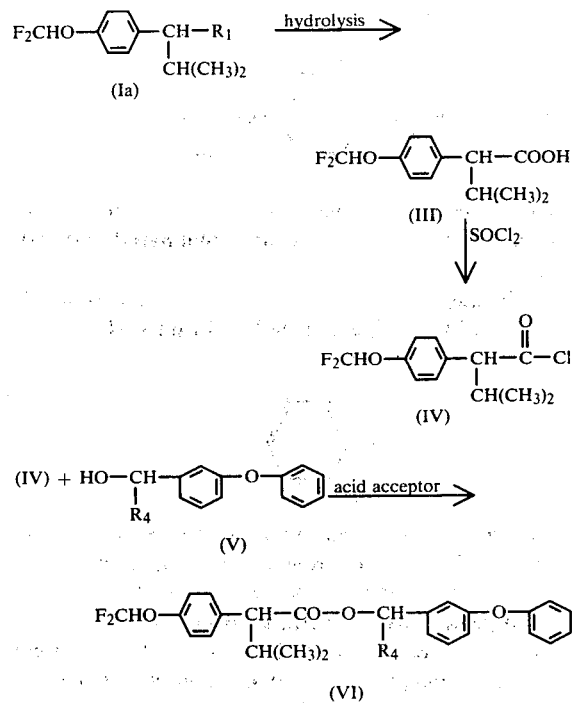

It is recognized that a chiral center is present in formula-(III) acid at the point where the isopropyl group is attached. Therefore, both d and l isomers are present. A chiral center is also present in formula-(VI) ester. It is further recognized that when $R_4$ is cyano, a chiral center is present in formula-(V) benzyl alcohol at the point of attachment of the $R_4$ group, allowing for an additional chiral center in formula-(VI) pyrethroid when $R_4$ is cyano, resulting in a total of two enantiomeric pairs for formula-(VI) pyrethroid.

Conveniently, a compound of formula-(Ia) may be prepared by the method of the present invention as follows:

One molar equivalent of a phenol of structural formula-(IIa)

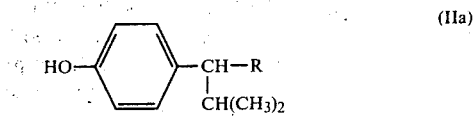

(IIa)

is admixed with and dissolved in a solvent mixture comprising: 2-propanol and acetone. Water is used in amounts from about 1740 to 2614 mol percent (preferably 2614 mol percent) relative to said phenol, and 10 mol percent of benzyltriethylammonium chloride (BTEAC) relative to said phenol. In the above reaction mixture the 2-propanol:acetone volume ratios are 1:1 to 1:3 and preferably 1:1. The combined volume of these two solvents is in the range of about 4 to 6 ml (preferably 4 ml) per gram of starting material. The system in which the reaction is to be run is then evacuated to remove any air present, and chlorodifluoromethane is then introduced under a pressure of about 0.4 to 2.5 kg $cm^{-2}$ (preferably 0.45 to 1.1 kg $cm^{-2}$). A few minutes after the start of the chlorodifluoromethane addition, one molar equivalent of aqueous sodium hydroxide (preferably 50% aqueous sodium hydroxide) is added quickly resulting in a mild exotherm. After the exotherm has subsided, the pressure under which the chlorodifluoromethane is added is readjusted if necessary to about 1.0 to 1.1 kg $cm^{-2}$. Over a period of one hour, two to three molar equivalents (preferably three molar equivalents) of chlorodifluoromethane are added, while simultaneously an additional three molar equivalents of aqueous sodium hydroxide (preferably 50% concentration) are slowly added approximately over the same period of time. The reaction temperature is maintained at a range of about 20° to 40° C. (preferably 30° to 35° C.). On completion of the additions, the reaction mixture is held for an additional period of about 0.1 to 6 hours or until said reaction is essentially complete (preferably from one to two hours). At the end of this sequence, the total amount of water added is present in the range of 2614 to 3482 mol percent (preferably 3482 mol percent) relative to the moles of starting material.

The thus obtained product of formula-(I) may be isolated from the reaction mixture by separating the organic phase which contains said product from the aqueous and solid phases.

The following Example further serves to illustrate the invention and are not intended to be limitative thereof.

EXAMPLE 1

Preparation of Methyl 2-[4-(difluoromethoxy)phenyl]-3-methylbutyrate

A mixture of methyl 2-(4-hydroxyphenyl)-3-methylbutyrate (0.2 to 0.3 mol), a solvent of 1:1 acetone:2-propanol mixture (used at the rate of 4 ml/g of the above compound), benzyltriethylammonium chloride (BTEAC; 0 to 10 mol percent) and water (1740 to 2614 mol percent) is stirred at 30° to 35° C. in a closed system. The system is evacuated and chlorodifluoromethane (3 molar equivalents) is introduced into the reaction mixture under a pressure of from 0.45 to 1.1 kg cm$^{-2}$ over a period of about 30 minutes to 1.0 hour. About 5 minutes after the start of the chlorodifluoromethane addition, one molar equivalent of 50.6% aqueous sodium hydroxide is added all at once (causing a slight exotherm). The slow addition of three molar equivalents of 50.6% aqueous sodium hydroxide commences and is completed in about the same period of time needed to add the chlorodifluoromethane. On completion of the additions the reaction mixture is stirred an additional 0 to 1 hour. The system is then evacuated to remove any unreacted chlorodifluoromethane from the reaction mixture. The organic layer is separated and evaporated under vacuum. The residue is dissolved in toluene. The toluene solution is washed with dilute aqueous sodium hydroxide and then with water. The solvent is then evaporated under vacuum to yield an orange liquid, the title product.

Several experiments are run by the above procedure, and the data thus obtained are summarized in Table I below. It can be clearly seen from Table I, that the combination of 1:1 acetone:2-propanol + 10 mol percent BTEAC affords the highest yields attained by utilizing the above procedure.

By the above procedure, but substituting ethyl 2-(4-hydroxyphenyl)-3-methylbutyrate, 2-(4-hydroxyphenyl)-3-methylbutyronitrile, 4-chlorophenol, p-cresol or 4-nitrophenol for methyl 2-(4-hydroxyphenyl)-3-methylbutyrate, 2-[4-(difluoromethoxy)phenyl]-3-methylbutyric acid ethyl ester, 4-chloro-α,α-difluoroanisole, α,α-difluoro-4-methylanisole or α,α-difluoro-4-nitroanisole can be prepared, respectively.

TABLE I

Preparation of Methyl 2-[4-(difluoromethoxy)phenyl]-3-methylbutyrate in the presence of BTEAC

| No. | Mol % water added at start | Mol % water added at end | ml of solvent per g of formula II 2-ProH** | ml of solvent per g of formula II acetone | Product BTEAC* mol percent | % crude | % purity | % yield |
|---|---|---|---|---|---|---|---|---|
| 1 | 2614 | 3482 | 2 | 2 | — | 83.04 | 86.1 | 71.5 |
| 2 | 2614 | 3482 | 2 | 2 | 2.5 | 83.87 | 86.4 | 72.5 |
| 3 | 2614 | 3482 | 2 | 2 | 10 | 92.21 | 85.7 | 79.0 |

*BTEAC = Benzyltriethylammonium chloride
**2-ProH = 2-propanol

What is claimed is:

1. A method for the preparation of a compound of structural formula-(I)

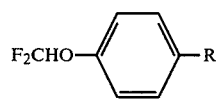
(I)

wherein R is C$_1$-C$_3$ alkyl, halogen, nitro or the moiety

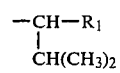

wherein R$_1$ is CN, COOR$_2$, OH or OR$_3$; R$_2$ is C$_1$-C$_3$ alkyl; R$_3$ is tosyl, mesyl or C$_2$-C$_4$ alkanoyl; comprising:

reacting one molar equivalent of a compound of structural formula-(II)

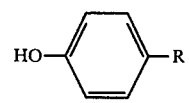
(II)

and R is as hereinabove defined, at a temperature of from 20° to 40° C. in the presence of 1740 to 2614 mol percent of water, 1:1 acetone:2-propanol used at a rate of 4 ml to 6 ml per gram of the compound of formula-(II), and 10 mol percent of benzyltriethylammonium chloride with two to three molar equivalents of chlorodifluoromethane added under a pressure of from 0.4 to 2.5 kg cm$^{-2}$ over a period of from 30 minutes to 1.0 hour while simultaneously adding to the pressurized reaction mixture an aqueous solution of four molar equivalents of an alkali metal hydroxide of sodium or potassium hydroxide over a 1 to 4 hour period, wherein the concentration of said aqueous solution is such that on completion of the addition the total amount of water added to the reaction mixture is from 2614 to 3482 mol percent; after the completion of the addition the reaction mixture is further maintained at the above pressure and temperature ranges for a period of from 0.1 to 6 hours or until said reaction is essentially complete.

2. A method according to claim 1, wherein 3 molar equivalents of chlorodifluoromethane are added over a 30 minute to 1.0 hour period at a pressure from about 0.4 to 1.1 kg cm$^{-2}$, at a temperature of from about 30° to 35° C., and further maintained at the above pressure and temperature ranges for about 1 to 2 hours; in the presence of 2614 mol percent water, 1:1 2-propanol:acetone used at a rate of 4 ml per gram of the compound of formula-(II); the alkali metal hydroxide is sodium hydroxide; and the total amount of water added to the reaction mixture is 3482 mol percent.

3. A method according to claim 2, wherein R is CH$_3$, Cl, NO$_2$ or

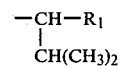

where R$_1$ is CN, COOCH$_3$ or COOC$_2$H$_5$.

4. A method according to claim 3 wherein said compound is methyl 2-[4-(difluoromethoxy)phenyl]-3-methylbutyrate.

5. A method according to claim 3, wherein said compound is ethyl 2-[4-(difluoromethoxy)phenyl]-3-methylbutyrate.

6. A method according to claim 3, wherein said compound is 2-[4-(difluoromethoxy)phenyl]-3-methylbutyronitrile.

7. A method according to claim 3, wherein said compound is 4-chloro-α,α-difluoroanisole.

8. A method according to claim 3, wherein said compound is 4-methyl-α,α-difluoroanisole.

9. A method according to claim 3, wherein said compound is 4-nitro-α,α-difluoroanisole.

* * * * *